United States Patent [19]

Yanase

[11] Patent Number: 4,634,006
[45] Date of Patent: Jan. 6, 1987

[54] BAG FOR MOTHERS MILK

[76] Inventor: Shozaburo Yanase, 2-20, Tsurigane-cho, Higashi-ku, Osaka, Japan

[21] Appl. No.: 677,557

[22] Filed: Dec. 3, 1984

Related U.S. Application Data

[63] Continuation-in-part of Ser. No. 561,975, Dec. 16, 1983, Pat. No. 4,600,104.

[30] Foreign Application Priority Data

Jun. 8, 1983 [JP] Japan .............................. 58-87257[U]

[51] Int. Cl.⁴ ...................... B65D 17/28; B65D 33/16
[52] U.S. Cl. .................................... 206/604; 383/44; 383/61; 383/91; 383/112; 383/113; 383/908
[58] Field of Search ................... 383/44, 35, 112, 113, 383/91, 61, 908; 215/11 E; 206/484, 604

[56] References Cited

U.S. PATENT DOCUMENTS 3,263,903  8/1966  Waller et al. .......................... 383/44
3,282,412  11/1966  Corella et al. ......................... 383/44

Primary Examiner—Stephen P. Garbe
Attorney, Agent, or Firm—Oblon, Fisher, Spivak, McClelland, & Maier

[57] ABSTRACT

A bag for mother's milk made of a laminated film or tube prepared through extrusion molding for containing mother's milk therein comprising a sealing portion provided on at least one side of the bag and extended across the extrusion direction and notches provided on the sealing portion for opening the sealing portion along the extrusion direction, while the bag is tightly sealed without any object therein, and a funnel-shaped reflux preventing member.

24 Claims, 26 Drawing Figures

BAG FOR MOTHERS MILK

CROSS-REFERENCE TO RELATED APPLICATION

The present application is a continuation-in-part of application Ser. No. 561,975 filed Dec. 16, 1983, now U.S. Pat. No. 4,600,104.

DETAILED DESCRIPTION OF THE INVENTION

The present invention relates to a bag for the preservation of mother's milk and, more specifically, it relates to a bag for mother's milk made of a laminated film or laminated tube prepared through extrusion molding for preserving the mother's milk in a frozen state. The "mother's milk" according to the present invention means breast milk—that is to say, milk from a woman's breast.

The bag is provided with a funnel-shaped reflux preventing member. This member is also to effect a milk flow guiding.

The bag for the preservation of the mother's milk is constructed such that it is supplied to users in the form of a hermetically or tightly sealed bag which contains substantially nothing in the inside of the bag. The users can easily open the sealed bag at one end for filling the mother's milk to the inside.

The importance of the mother's milk for the sake of babies'health has been re-estimated in recent years, particularly from a dietetical and immunological points of view.

A refrigerator with a freezing chamber has been spread widely to general homes whereby it has become possible to suck the milk by a breast pump as disclosed in U.S. Pat. No. 3,977,405 into a suitable container and preserve it in the frozen state formed within the freezing chamber. Then, the frozen milk can be thawed at any time and supplied to an infant by the use of the known baby's bottle or sucker even in a case where the mother can not directly give her milk to her infant.

The container has to be kept in a sterilized state until it is filled up with the milk.

By the way, it is required for the container of this type intended to be used for preserving the mother's milk in a frozen state within the freezer that the container can be kept at a sterilized state until it is served for filling the mother's milk therein. In addition, it is necessary that the container can be used conveniently and is provided conveniently to the user. Further, the container is, desirably, disposable after the use.

Thin flexible bags made of synthetic resin or the like have heretofore been used as the container for the preservation of the mother's milk. However, since most of such bags are usually opened at one end thereof, they involve a difficulty in keeping the inside of the bag in a sterilized state.

The first objective of the present invention is to provide a bag for mother's milk which is made of a laminated film or laminated tube in order to preserve the mother's milk contained in the bag in a frozen state, usually hermetically sealed until the bag is actually used for the preservation of the milk therein and can be opened at one end thereof to insert the milk in the bag without using particular means such as scissors. The hermetically sealed bag is exposed to gamma ray irradiation for sterilization of the inside and can be kept at a sanitary state.

A second objective of the present invention is to provide a bag for the preservation of the mother's milk made of a laminated film or laminated tube in which the inner layer of the bag tends to elongate more readily than the outer layer of the bag for easier filling of the mother's milk in the bag when it is opened. Accordingly, the opening periphery of the bag is turned or bended outwardly near the opened portion due to the greater elongation rate of the inner layer than that of the outer layer to facilitate the filling of the mother's milk in the bag.

A third objective of the invention is to provide a bag for mother's milk made of a laminated film or tube having a funnel-shaped milk flow guiding and reflux preventing member to facilitate milk's flowing into the desirable portion within the bag and to prevent reflux.

A fourth objective of the present invention is to provide a bag for the preservation of the mother's milk which is further combined with means for closing said open portion of the bag again after the bag has been opened and the mother's milk has been filled in the bag. In addition, closure for the open portion of the bag by the above-mentioned closing means can further be facilitated by preliminarily closing the bag at the position near the level of the milk in the bag with a preliminary closing means prior to the closure of the opened portion by said closing means.

In one aspect of the present invention, there is provided a bag for the preservation of the mother's milk made of a laminated film or laminated tube prepared by extrusion molding, wherein said bag comprises a sealing portion(s) provided on a one or more sides of the bag and extended in the transverse direction to the direction of said extrusion, and at least one notch provided on the sealing portion and directed in the same or opposite direction of said extrusion for opening the one end of the bag along or opposite to the direction of extrusion, the bag being hermetically or tightly sealed.

Preferably, the bag contains substantially nothing in the inside thereof in the tightly sealed up state before the bag is actually used.

The foregoing and other features, as well as advantages, of the present invention will become clearer from the following descriptions of preferred embodiments thereof in conjunction with the accompanying drawings, in which FIG. 1 is an explanatory view showing a preferred embodiment of a bag for the preservation of the mother's milk according to the present invention in which one end of the bag is turned back for showing the lower surface, as well as the upper surface thereof;

Figure 1:
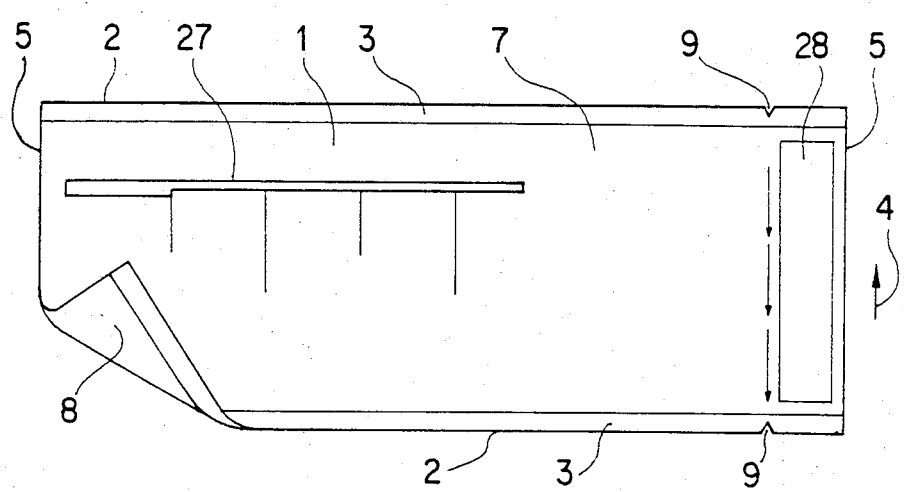

The bag for the preservation of the mother's milk is made of a laminated film or laminated tube obtained from an extrusion molding of a thermoplastic resin, wherein said bag comprises sealing portion(s) provided on one or more sides of the bag and extended in the transverse direction to the direction of said extrusion, and notches provided on the sealing portion(s) at the direction of said extrusion in order to open the bag along the direction of extrusion, the bag being hermetically or tightly sealed while containing substantially nothing therein, and the bag can readily be torn to open induced by the notches along or opposite to the extrusion direction.

Mother's milk is collected by using a breast pump such as is disclosed in U.S. Pat. No. 3,977,405 and the mother's milk contained in the breast pump can be put into the bag through said open portion as described above. The bag thus containing the mother's milk therein is closed at the open portion by the closing means and then placed in a freezer or a freezing chamber and said milk is preserved in a frozen state, for example, at a temperature below −18° C. The closing means comprises at least one elongate plate member made of thick paper, board or plastic sheet etc. When the closing means comprises three elongate plates, first, second and third elongate plates, one longer edge of the first elongate plate is foldably connected to the mating longer edge of the second elongate plate, and one shorter edge of the first elongate plate is foldably connected to the mating shorter edge of the third elongate plate. The bag can surely be closed with the closing means by folding the third elongate plate over the first elongate plate to hold the open portion of the bag between the first and the second elongate plates, further folding the second elongate plate over the third elongate plate and, thereafter, winding the portion near the open portion of the bag around the three folded elongate plates by the several turns. Thereafter, an adhesive tape is appended at the closed portion of the bag to closely seal and secure the portion with ease. Each of the three elongate plate members has preferably the same size.

A preliminary closing member such as a clip may be used for preliminarily closing the bag at the position near the level of the milk in the bag prior to the above-mentioned closure by means of the closing means. This can surely prevent the mother's milk contained in the bag from leaking externally and can much facilitate or aid the subsequent closure of the open portion made by the closing means, and also can facilitate a removal of air remaining in the bag.

The closing means 37 (shown in FIG. 7) may be made of two parts 38 and 39, each of which is an elongate strip foldable at the center. Either one thereof is removably attached to the bag near notches before opening the bag through the notches in order to easily fill up with milk. The other one thereof is removably attached to the bag at a folded open end in order to fix the end after having been filled with the milk.

In the drawings, a bag for the preservation of the mother's milk generally shown by the reference numeral 1 is made of a laminated tube 10 prepared from extrusion molding by cutting the tube in the transverse direction to the extruding direction at every predetermined length and sealing or welding each of cut edges 2, 2 by means of heat seal. The sealing portions or the welding portions 3, 3 thus formed for sealing up the bag 1 are extended in the direction substantially perpendicular to the direction of an arrow 4 which represents the extruding direction of the laminated tube 10. The bag 1 is of a generally rectangular shape defined with the cut edges 2, 2 and lateral edges 5, 5 as both ends. The lateral edges 5, 5 are already closed upon molding of the laminated tube 10 and defined by folding the lateral ends of the laminated tube 10 between pinch rollers 6, 6 (refer to FIG. 4). In other words, the bag 1 comprises an upper surface 7 and a lower surface 8 integrally connected to each other at the lateral edges 5, 5 upon molding and is hermetically or tightly sealed by sealing the upper surface 7 and the lower surface 8 at the sealing portions or welding portions 3, 3. Although a small amount of air may be left within the bag 1 after said sealing step, it is preferred that the bag is sealed up so tightly that it contains substantially nothing in its inside. Then, the sealed bag 1 is exposed to gamma ray irradiation in order to sterilize the inside of the bag 1.

Notches 9, 9 directed along and opposite to the direction of the arrow 4 are provided on the sealing portions or the welding portions 3, 3 at a position close to one of the lateral edges 5.

Figure 3:
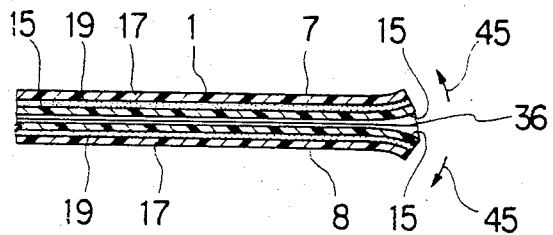
FIG. 3 is an enlarged cross sectional view taken along line III—III in FIG. 2.
Figure 4:
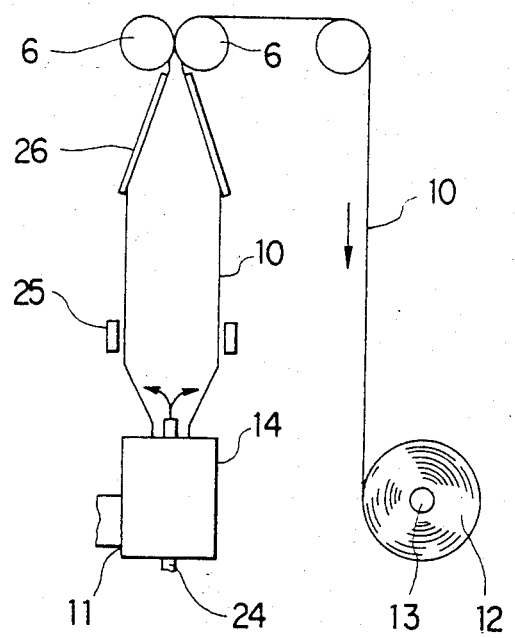
FIG. 4 is an explanatory view of the apparatus for producing a laminated tube.
Figure 5:
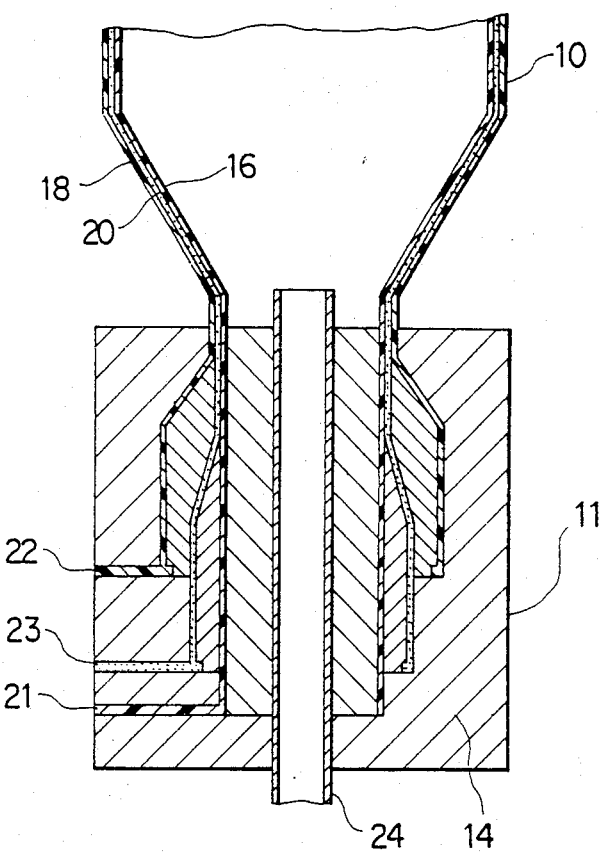
FIG. 5 is an enlarged cross sectional view of a part of the apparatus shown in FIG. 4.

As shown in FIG. 4, a molding apparatus for producing the laminated tube 10 comprises an extruder 11 and a take-up apparatus 12 for taking-up the laminated tube 10 extruded from the extruder 11 through pinch rollers 6, 6. The laminated tube 10 extruded from the extruder 11 is inflated into a thin tubular laminate by the air blown into the tube through a conduit 24 and then taken-up around a take-up roller 13 of the take-up apparatus 12 while being pulled so as to slightly elongate in the extruding direction corresponding to the arrow 4 by the pinch rollers 6, 6 and then folded between the rollers. The laminated tube 10, of which plurality of the bags 1 are made, comprises a first layer 16 as an inner layer 15 of the bag 1, a second layer 18 as an outer layer 17 of the bag 1, and an adhesive layer 20 as an intermediate layer 19 (adhesive layer) between the inner layer 15 and the outer layer 17 (refer to FIG. 3 and FIG. 5). Correspondingly, the die 14 in the extruder 11 comprises, as shown in FIG. 5, passageways 21, 22, and 23 for molten thermoplastic resins forming the first layer 16, the second layer 18, and the adhesive layer 20 respectively. The conduit 24 extended in the axial direction in the die 14 is communicated with a pressurized air source (not shown) for inflating the laminated tube 10. A cooling device 25 is disposed between the die 14 and the pinch rollers 6, 6, and a guide plate 26 is disposed at the upstream of the pinch rollers 6, 6 for guiding the laminated tube 10 to the gap between the pinch rollers 6, 6 so that the laminated tube 10 may preferably be folded by the pinch rollers 6, 6.

It is necessary that the inner layer 15 for the bag 1 forms a good barrier against moisture transmission, is water proof, and is flexible, as well as that it should be chemically stable having no substantial effect on the mother's milk to be contained in the inside of the bag. Accordingly, a polyethylene is employed, for instance, as the thermoplastic resin material forming the first layer 16 of the tube 10. On the other hand, it is necessary that the outer layer 17 of the bag 1 has heat and cold resistant properties and that it be flexible, as well as that it should be less than gas permeable and have oil-resistance and chemical stability. Accordingly, a nylon is employed, for instance, as the thermoplastic resin material forming the second layer 18 of the tube 10. Furthermore, as described below, it is required for the inner layer 15 that it has a larger elongation rate than that of the outer layer 17. This requirement can be satisfied well by forming the inner layer 15 from polyethylene and the outer layer 17 from nylon. The intermediate layer 19 is an adhesive layer for bonding the inner layer 15 with the outer layer 17. The bag 1 is formed as a transparent or translucent and thin body.

An appropriate scale 27 is printed on the upper surface 7 of the bag 1 for measuring the volume of the mother's milk contained in the bag 1, by which the user of the bag 1 can easily recognize the amount of the mother's milk contained in the bag 1. Furthermore, notices concerning how to use the bag 1 or the like are printed on the upper surface 7. For instance, notices indicating how to open the bag 1 are printed on a space 28 between the lateral edge 5 and the notches 9, 9 of the bag 1.

Figure 2:
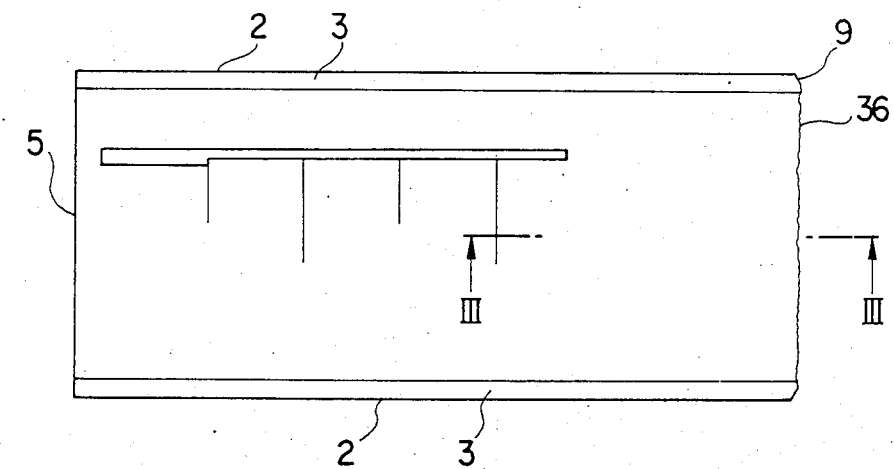
FIG. 2 is a plan view of the bag shown in FIG. 1 after opening the bag.

The hermetically sealed bag 1 for the preservation of the mother's milk can be easily opened by tearing it off at the notch 9 formed at the welding portions 3, 3 (refer to FIG. 2).

Figure 6:
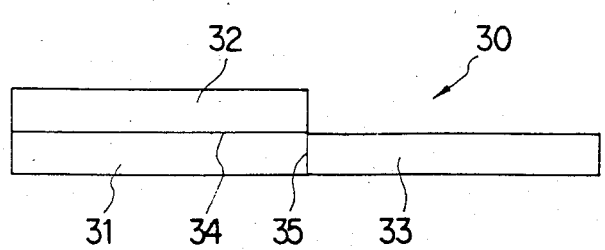
FIG. 6 is a plan view of a specific embodiment of a closing means.

FIG. 6 shows a closing means 30 for closing the bag 1 opened at one end 36 through which the mother's milk is filled in the bag 1. The closing means 30 comprises three elongate plates 31, 32 and 33 each of a rectangular configuration. Each of the plates 31, 32 and 33 is of substantially the same size, has a length greater than the width or the size between the sealing portions or the welding portions 3, 3 of the bag 1, and is made of thick paper such as a cardboard or a plastic sheet. A longer folding line 34 is formed between the longer edge of the plate 31 and the mating longer edge of the plate 32, so that the plates 31 and 32 are foldably connected to each other by way of the longer folding line 34. A shorter folding line 35 is formed between the shorter edge of the plate 31 and the mating shorter edge of the plate 33, so that the plates 31 and 33 are foldably connected to each other by way of the shorter folding line 35.

Figure 7:
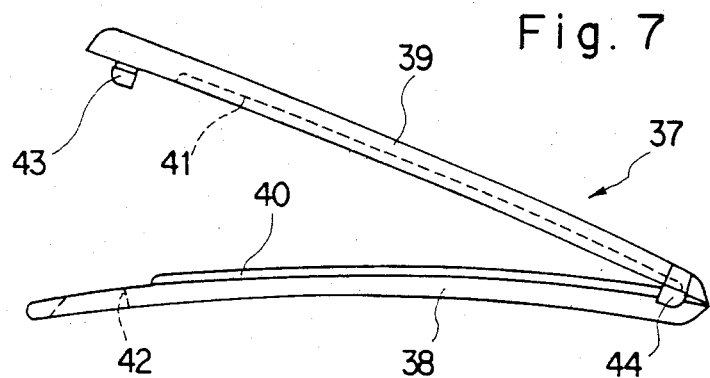
FIG. 7 is a side view of a preliminary closing means.
Figure 8:
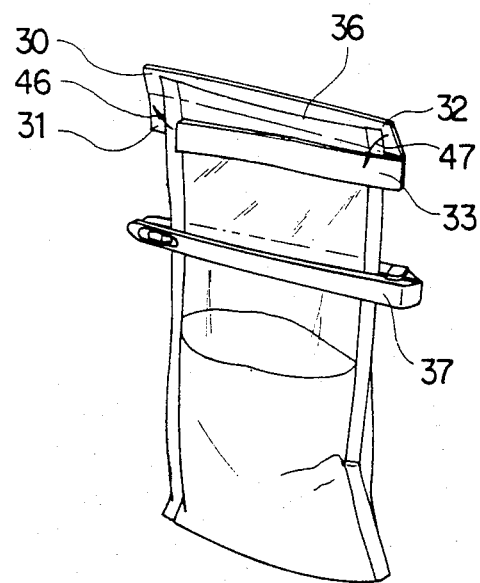
FIG. 8 and FIG. 9 are explanatory views illustrating a method for closing the open portion of the bag.

FIG. 7 shows a preliminary closing means 37 for preliminarily closing the opened bag at the position near the level of the milk in the bag 1 before closing the open portion 36 by means of the closing means 30. The preliminary closing means 37 comprises a plastic clip composed of a lower clipping member 38 and an upper clipping member 39 hinged at one end to each other. An elongate ridge 40 and an elongate groove 41 in a complementary shape are provided respectively on the opposing surfaces of the lower clipping member 38 and the upper clipping member 39. The length for the ridge 40 and the groove 41 is greater than said width of the bag 1. A conversely tapered aperture 42 is formed in the other end of the lower clipping member 38, and a protrusion 43 is formed on the other end of the upper clipping member 39 for insertion into the aperture 42 to keep both of the clipping members 38 and 39 in a closed position as shown in FIG. 8. The lower clipping member 38 has a curved configuration for providing the same with a biasing tendency relative to the upper clipping member 39, so that upon disengaging the aperture 42 from the protrusion 43, both of the clipping members 38 and 39 are shifted to open positions as shown in FIG. 7. Guide pieces 44 are integrally connected on both sides at one end of the upper clipping member 39 for guiding the lower clipping member 38 therealong.

In this structure, when the bag 1 is clipped by means of the preliminary closing means 37 at the position near the level of the mother's milk in the bag 1, the bag 1 is surely clipped at said position between the elongate ridge 40 and the elongate groove 41, thereby preventing the mother's milk contained in the bag 1 from leaking externally.

The total thickness of the layers 15, 19 and 17 is 50–150 $\mu$m and, preferably, 75–90 $\mu$m. The thickness of the inner layer 15 is 20–50 $\mu$m, preferably, 25–30 $\mu$m; the thickness for the intermediate layer 19 is 15–50 $\mu$m, preferably, 25–30 $\mu$m; and the thickness for the outer layer 17 is 15–50 $\mu$m, preferably, 25–30 $\mu$m.

The inner layer 15 as the first layer 16 may be made of transparent low density polyethylene, transparent medium density polyethylene, transparent high density polyethylene, transparent linear low density polyethylene, or transparent polypropylene.

The outer layer 17 as the second layer 18 may be made of transparent nylon 6, transparent nylon 6—6, transparent copolymer of nylon 6 and nylon 6—6, transparent polymer or copolymer of vinylidene chloride resin, or transparent Eval.

The intermediate layer 19 as the adhesive layer 20 may be made of a modified polyolefin resin.

In the use of the bag 1 for the preservation of the mother's milk having the foregoing structure, one end of the bag is opened through the notches 9, 9 for filling the bag 1 with the mother's milk which has been collected by a breast pump such as disclosed, for instance, in U.S. Pat. No. 3,977,405.

The bag 1 is provided with the sealing portions or the welding portions 3, 3 in the direction perpendicular to the direction of the arrow 4, that is, the direction of extruding the laminated tube 10 and formed with the notches 9, 9 in the vicinity of one of the edges 5, 5 at the sealing portion or the welding portions 3, 3. Since the notches 9, 9 are oriented respectively along and opposite to the direction of the arrow 4, the bag 1 can be easily opened at one end thereof by picking-up two portions near one of the notches and pulling one of said two portions in the direction toward the other of the notches, the two portions being both side portions of the notch 9 on the sealing portion or the welding portion 3. Since the laminated tube 10 has been pulled so as to be slightly elongated in the extruding direction by the pinch rollers 6, 6 upon molding of the laminated tube 10, the bag 1 can be rather easily torn or broken in the direction perpendicular to the arrow 4. Accordingly, it is not necessary to use scissors or the like to open the bag 1, and the open portion 36 of the bag 1 can be prevented from contamination by scissors or the like.

In addition, since the inner layer 15 is made of material (for example, polyethylene) with a greater elongation rate than that of the outer layer 17 (which is made, for example, of nylon), the inner layer 15 is lengthened more than the outer layer 17, upon tearing the one end of the bag 1 through the notch 9, whereby the upper surface 7 and the lower surface 8 are turned or bended outwardly in the direction of the arrows 45 at the opened end 36 of the bag 1, as shown in FIG. 3. This can remarkably facilitate the operation of filling the mother's milk through the open portion 36 to the inside of the bag 1. Specifically, the mother's milk contained in the breast pump can be easily put into the bag 1 by inserting the open end of the breast pump into the open portion 36 where the upper surface 7 and the lower surface 8 are outwardly turned so as to make the surfaces be apart from each other in the direction of the arrow 45. The breast pump and the periphery of the open end thereof have to be previously kept free from any contamination.

Figure 9:
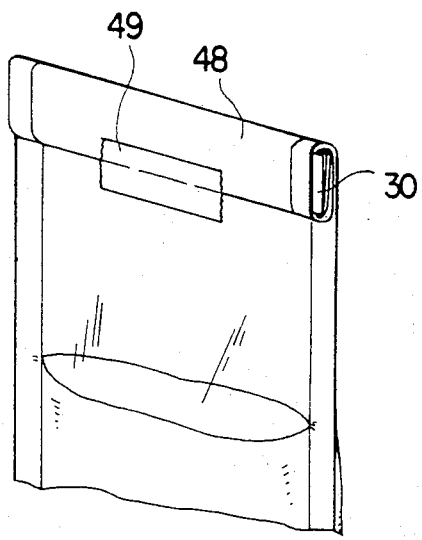
Figure 10:
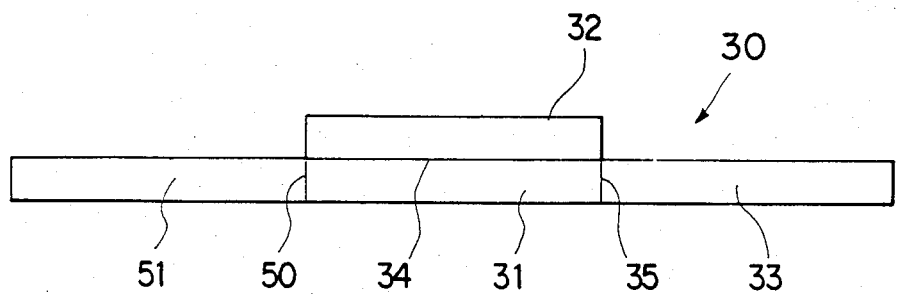
FIG. 10 is a plan view of another specific embodiment of the closing means.

After filling the mother's milk in the bag 1, the portion of the bag 1 which is situated slightly above the level of the milk in the bag 1 is clipped by the preliminary closing means 37 and air remaining in the bag 1 is removed from the inside of the bag 1. Thereafter, the bag is closed by the closing means 30 (refer to FIG. 8). The elongate plate 33 is folded over the elongate plate 31 along the shorter folding line 35 in the direction of the arrow 46 so as to put the portion near the open portion 36 of the bag 1 between the plates 31 and 33. Then, the elongate plate 32 is further folded thereover along the longer folding line 34 in the direction of the arrow 47 so as to put the open portion 36 between the plates 32, 33. Thereafter, the portion near the open portion 36 of the bag 1 is wound by several turns around the three plates 31, 32 and 33 folded to each other, whereby the bag 1 can surely be closed (refer to FIG. 9). Then, the adhesive tape 49 is appended over the closed portion 48 so that the closed portion 48 can be easily secured or fixed. The adhesive tape 49 comprises, desirably, a non-toxic and cold-working tape comprising a substrate made of a plastic film such as a polyester resin having predetermined strength, flexibility, and cold resistance. Adhesives not solidifying at low temperature are disposed on the substrate. In the above operation, it is possible to facilitate the removal of air remaining in the bag 1 owing to the preliminary closing means 37.

The bag 1 has an indication on the outer surface thereof such as the date of filling or the like and can be preserved in the frozon state within the freezing chamber of a refrigerator or the like. The milk thus preserved in the frozen state can be taken out as desired from the freezing chamber 1 and can easily be thawed by immersing the bag into water. The thawed milk is transferred from the bag 1 into a baby bottle or sucker, through which it can be easily served to the infant. The bag 1 and the closing means 30 are discarded or thrown away after use. U.S. Pat. No. 3,977,405 as described above discloses a breast pump equipped with a baby's bottle by which the milk can be served to the baby.

Although the closing means 30 comprises three elongate plates 31, 32 and 33 each of the same size and having the length greater than the width of the bag 1 in the above embodiment, the length for the elongate plate 33 may be made shorter. Said closing means may be made of two elongate plates 31, 32 by omitting the plate 33 or may be made of only one elongate plate 31 by omitting the plate 32 and 33. Alternatively, another elongate plate 51 may be provided foldably to the shorter edge of the elongate plate 31 by way of a shorter folding line 50, so that the elongate plates 33 and 51 may be overlapped to each other on the elongate plate 31. The length for the elongate plate 51 may be shorter than the width for the bag 1. The closing means may be made of thin plastic material.

Instead of using such closing means 30, the open side 36 of the bag 1 may be closed simply by an annular rubber string or the like.

Further, while the bag 1 is made of the inner layer 15, the outer layer 17, and the intermediate layer 19 as the adhesive layer in the above embodiment, the bag 1 may be made of two layers by using known methods of bonding the inner and the outer layers directly together.

Figure 11:
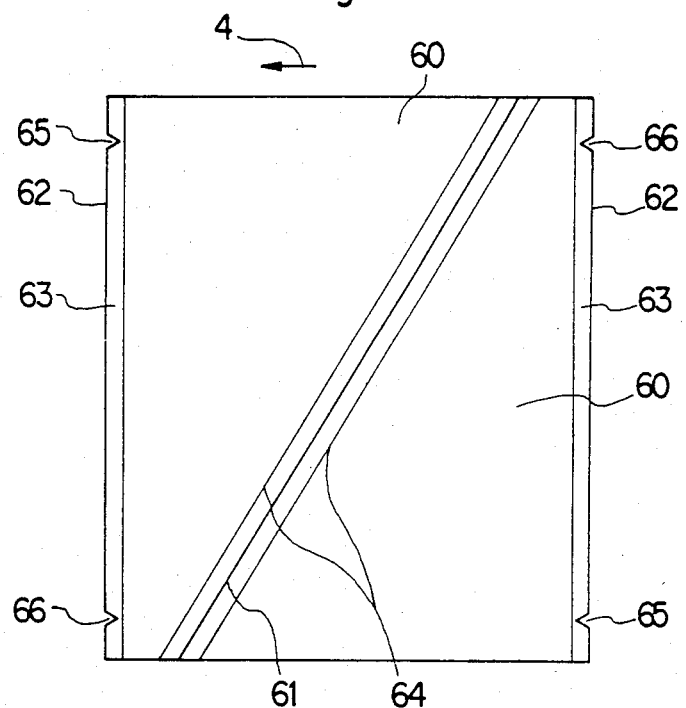
FIG. 11 is a plan view of another preferred embodiment of the bag for the preservation of the mother's milk according to the present invention.

In addition, although the bag 1 is formed as a rectangular shape in the above embodiment, the bag may be in a triangular shape or in a trapezoidal shape. FIG. 11 shows two bags cut out from the laminated tube 10 in which bags 60, 60 can easily be separated from each other along an oblique cutting line 61. Sealing or welding portions 63, 63 are formed along cut edges 62, 62 extending in the perpendicular direction to the direction of extruding the laminated tube 10 as shown by the arrow 4, and oblique sealing or welding portions 64, 64 extending along the cutting line 61 between the sealing or welding portions 63, 63. Each of the bags 60 is formed so as to be hermetically sealed between the sealing or welding portion 63 and the oblique sealing or welding portion 64, and notches 65, 66 are formed to the upper and lower end for each of the bags 60. Upon opening the bag 60, the bag is torn at one end thereof induced by the notch 65. After filling the mother's milk in the bag 60, the open portion of the bag 60 can be easily closed by the preliminary closing means 37 and the closing means 30. The notch 66 is formed for opening the other end of the bag 60 when milk preserved within the bag 60 in a frozen state is transferred into the baby's bottle after thawing. Since the other end of the bag 60 opened through the notch 66 is tapered on the lower side, the mother's milk in the bag 60 can easily be transferred into the baby's bottle. A notch may also be formed in the other end opposing to the open portion 36 of the bag 1 in the previous embodiment so as to open the other end through the notch and transfer the mother's milk in the bag 1 into the baby's bottle.

Figure 12:
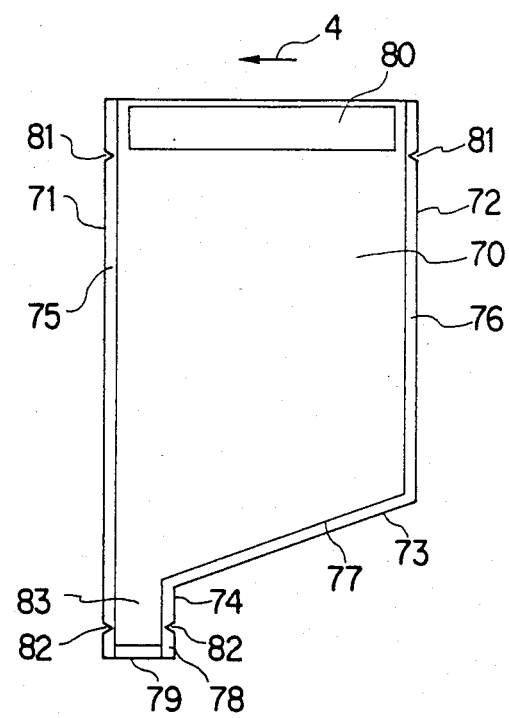
FIG. 12 is a plan view of a further embodiment of the bag for the preservation of the mother's milk according to the present invention.

FIG. 12 shows a bag 70 which is a further modified embodiment of the bag 1. The bag 70 is formed from the laminated tube 10 by cutting the tube along both of cut edges 71, 72 and further cutting along an oblique edge 73 extended obliquely from the lower end of the cut edge 72 and a downward edge 74 extended from the lower end of the oblique edge 73 downwardly substantially in the perpendicular direction to the arrow 4. The bag 70 is hermetically sealed by forming sealing or welding portions 75, 76, 77 and 78 along the cut edges 71, 72, the oblique edge 73 and the downward edge 74. A sealing or welding portions 79 extended between the sealing or welding portions 75 and 78 may be provided on the lower end of the bag 70. Notches 81, 81 are formed on the upper end of the sealing or welding portions 75, 76 at positions lower than a space 80 which corresponds to the space 28, while notches 82, 82 are formed on the lower ends of the sealing or welding portions 75, 78. One of the notches 81, 81 or one of the notches 82, 82 may be omitted. The notch 81 is so formed as to open the upper end of the bag 70 upon filling the mother's milk into the inside of the bag 70. The notch 82 is so formed as to open the lower end of the bag 70 upon transferring the mother's milk in the bag 70 into the baby's bottle. The positions for the downward edge 74 and the sealing or welding portion 78 are selected so as to define the outlet port 83 between the sealing or welding portions 75 and 78, in such a way that the size of the port 83 is slightly smaller than the diameter for the opening end of the baby's bottle. The notices concerning opening the upper end of the bag 70 through the notch 81 are printed on the space 80, and a scale is printed on the upper surfaces of the bag 70 in a manner similar to that as in the bag 1. Similar printings may be also applied on the bag 60.

Figure 13:
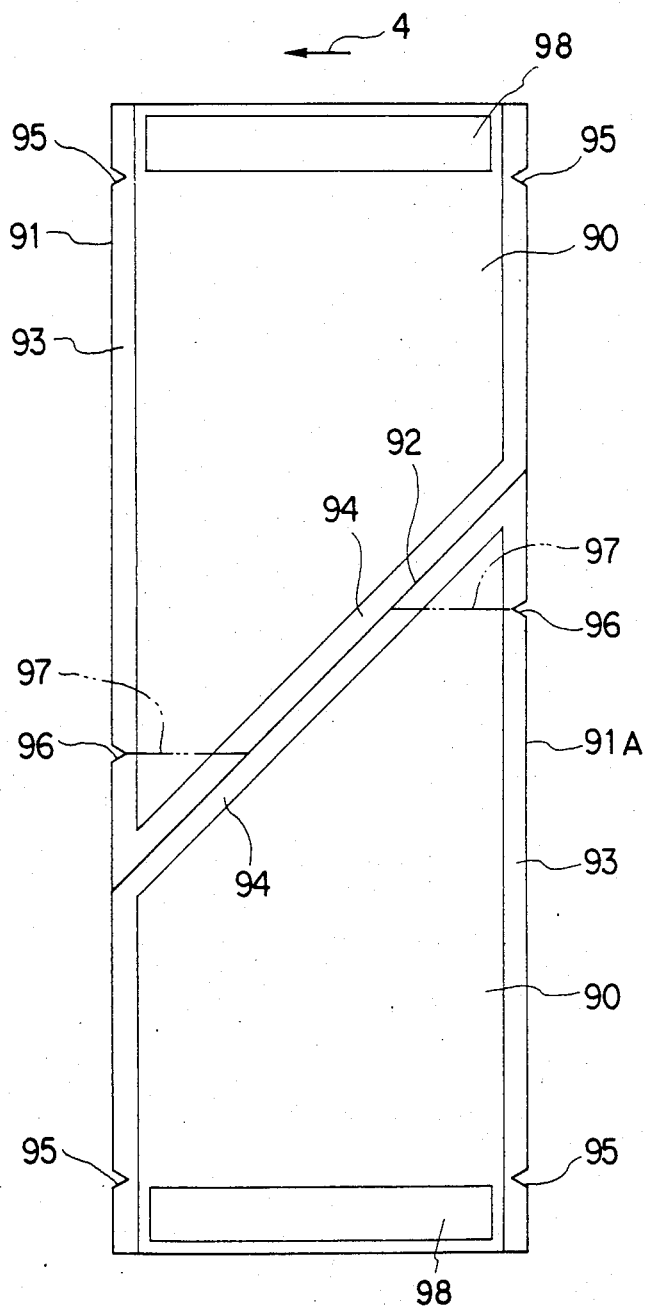
FIG. 13 is a plan view of a still further embodiment of the bag for the preservation of the mother's milk according to the present invention.

FIG. 13 illustrates two bags 90, 90 which are of the same trapezoidal shapes and can be easily separated from each other along an oblique cutting line 92. Welds 93, 93 are formed along cut edges 91, 91A extending along the direction perpendicular to the extrusion direction of the tube 10 as shown by the arrow 4, and oblique welds 94, 94 extending along the cutting line 92 between the welds 93, 93. Each of the bags 90 is so formed as to be tightly sealed between the weld 93 and 94, and notches 95, 96 are formed on the upper and lower sides for each of the bags 90. When opened, the bag is torn at the notch 95. After filling the bag 90 with the milk, the open side can be easily closed by the preliminary closing means 37 and the closing means 30. The notch 96 is formed in order to open the other side of the bag 90 along a line 97 when the milk preserved within the bag 90 is transferred into the baby bottle or sucker after thawing. Since the bag 90 is tapered on the lower side, the milk can be easily poured out from the bag 90 into the sucker. A set of necessary indications may be printed on the space 98 of the bag 90. If desired, a scale may be also provided on the upper surface of the bag 90.

The bags 1, 60, 70 and 90 can be modified as shown in FIGS. 14 to 18 and FIGS. 21 to 26. A pair of welds 101 and 102 is formed at an inner part of the bag 1 spaced from the notches 9 and 9. The flowing passage within the bag is narrowed at the location of welds 101 and 102 for guiding the milk flow within the bag since the welds 101 and 102 works as a milk flow guiding and reflux preventing member.

The funnel-shaped member consists of a pair of integral partitions, each of which is formed by welding the inner layer 15, the intermediate layer 19, outer layer 17, and the weld portions 3, 3 together.

The funnel-shaped member is located near notches 9 and 9 of the open end of the bag.

The funnel-shaped member facilitates guiding any flow of the milk into the bag and also effects preventing of any reflux flow of milk to the outside.

Figure 19:
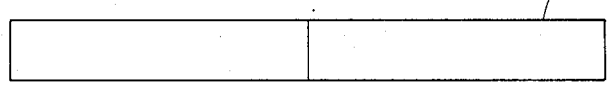
FIG. 19 is a plan view of another embodiment of the closing means.
Figure 20:
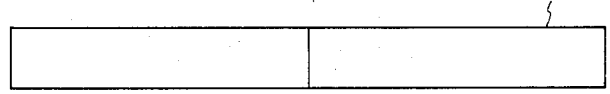
FIG. 20 is a plan view of another embodiment of the closing means which is used in combination with the means as shown in FIG. 19.
Figure 21:
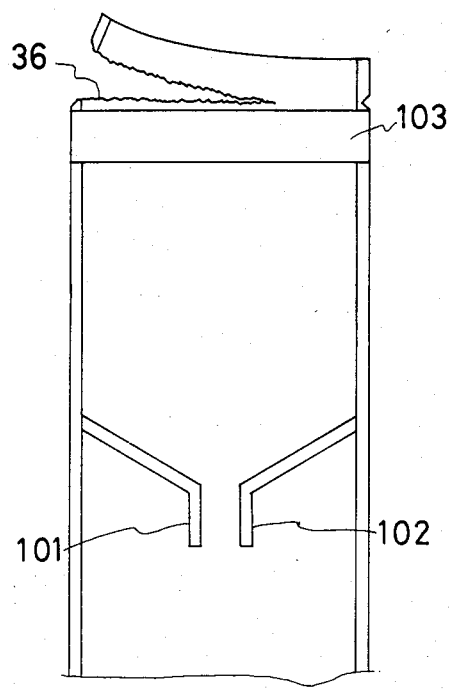
FIGS. 21 to 23 are explanatory views illustrating steps of filling the bag with the milk and closing the bag thereat.
Figure 22:
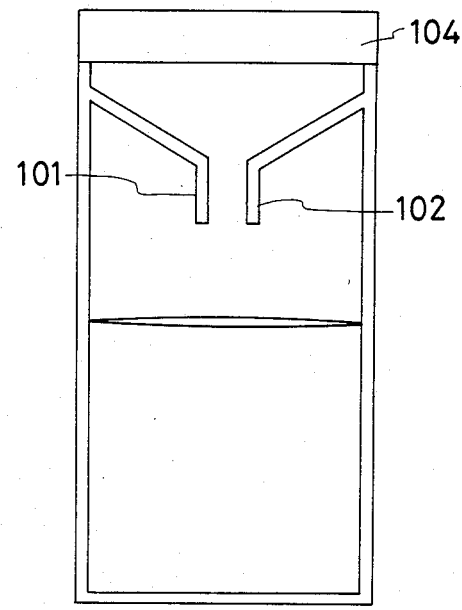

The bag 1 with the welds 101 and 102 to the outer surface of which a closing means 103 as shown in FIG. 19 is firmly adhered near the notches 9 and 9 is opened by tearing off an opening end of a minor part of the bag 1 along the notches 9 and 9 as shown in FIG. 21.

Soon after the bag has been opened, the bag 1 is filled up with milk.

The top end of the bag is rolled up several turns together with means 103.

Figure 23:
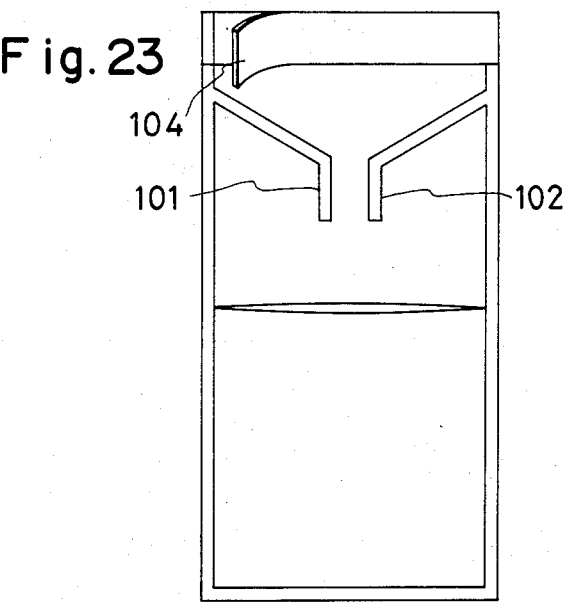

To the rolled up top end of the bag another closing member 104 is applied as shown with FIG. 23, firmly fixing the larger part of the surface of the rolled up top end of the bag.

The means 103 is made of cardboard or the like so that a user can write some notes (such as the date of filling or the like) on the means 103. The means 104 is preferably made of any transparent material, for example, a thermoplastic resin material. Thus, the user can read the notes on the means 103 through the transparent means 104.

The means 104 can be made of cardboard or the like on which the user can write directly.

It is desirable that the means 103 is made of hard material, (for example, cardboard or the like), since the hard means 103 works as a means for supporting the side 36 to be opened when the bag 1 is filled with the milk.

Figure 18:
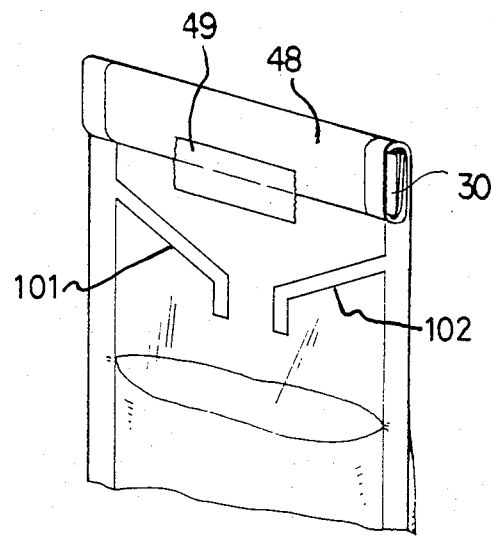
FIG. 18 is an explanatory view of showing the bag as shown in FIGS. 14 and 15 which is closed at the open side.

The bag 1 with the welds 101 and 102 can be also closed as shown in the above after filling of the milk (see FIG. 18).

Figure 24:
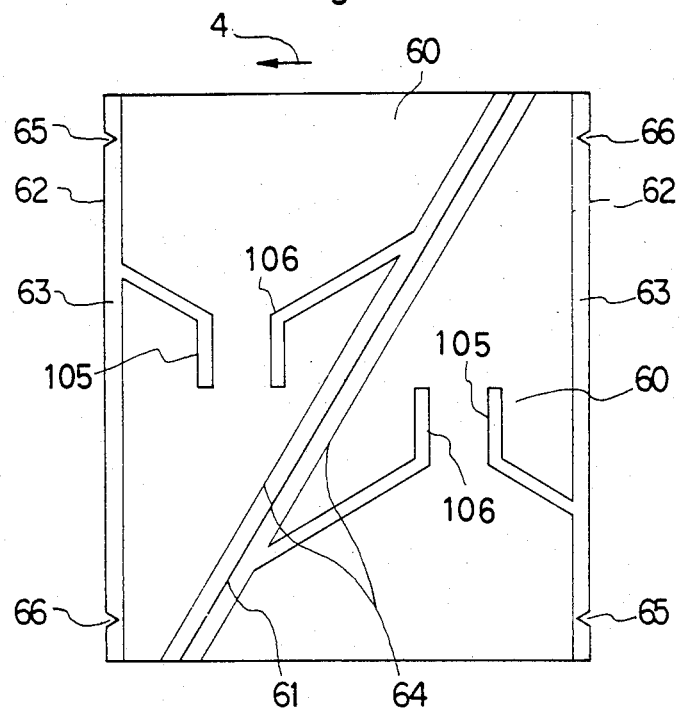
FIG. 24 is a plan view of another preferred embodiment of the bag according to this invention.

A pair of welds 105 and 106 is provided at an inner part of the bag 60 near the notches 65 as shown in FIG. 24.

Figure 25:
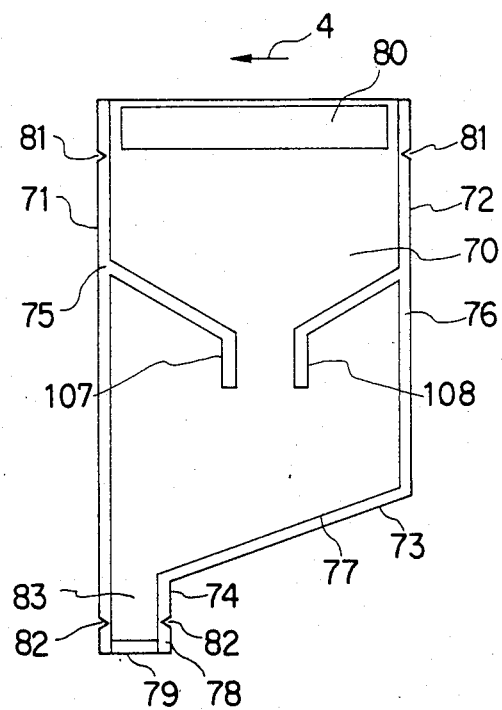
FIG. 25 is a plan view of another embodiment of the bag according to this invention.

A pair of welds 107 and 108 is made at an inner part of the bag 70 near the notches 81 and 81 as shown in FIG. 25.

Figure 26:
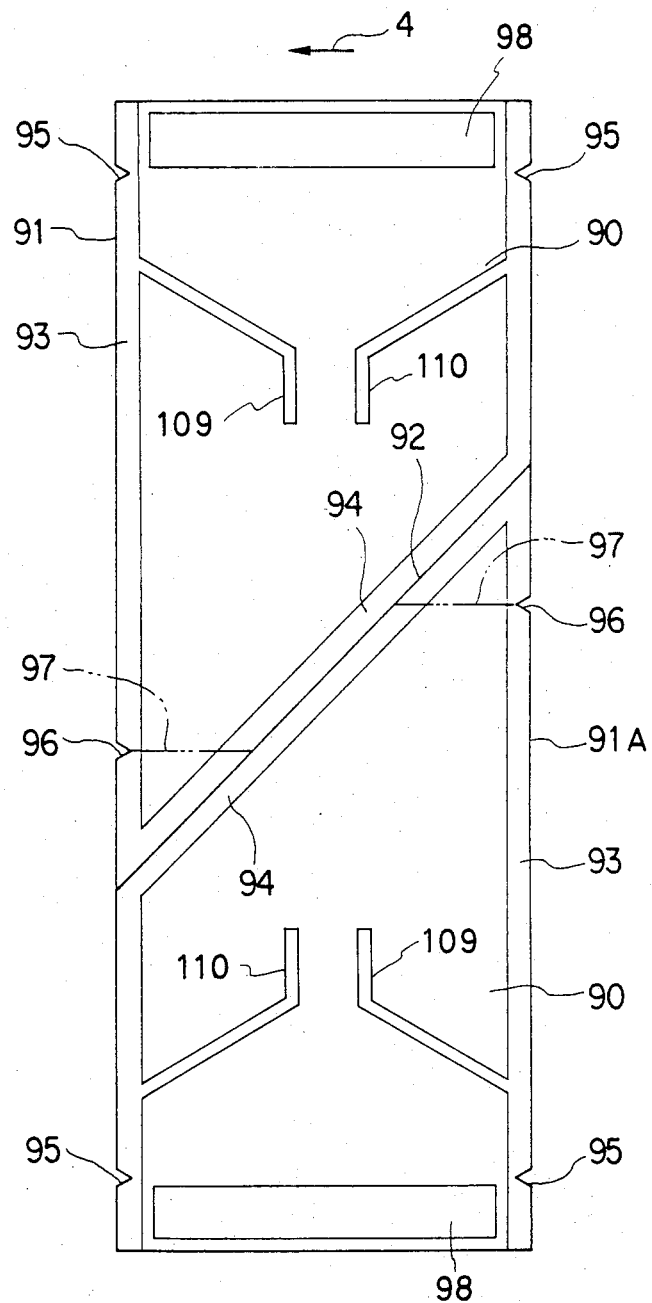
FIG. 26 is a plan view of another embodiment of the bag according to this invention.

A pair of welds 109 and 110 is prepared at an inner part of the bag 90 near the notches 95 and 95 as shown in FIG. 26.

Figure 14:
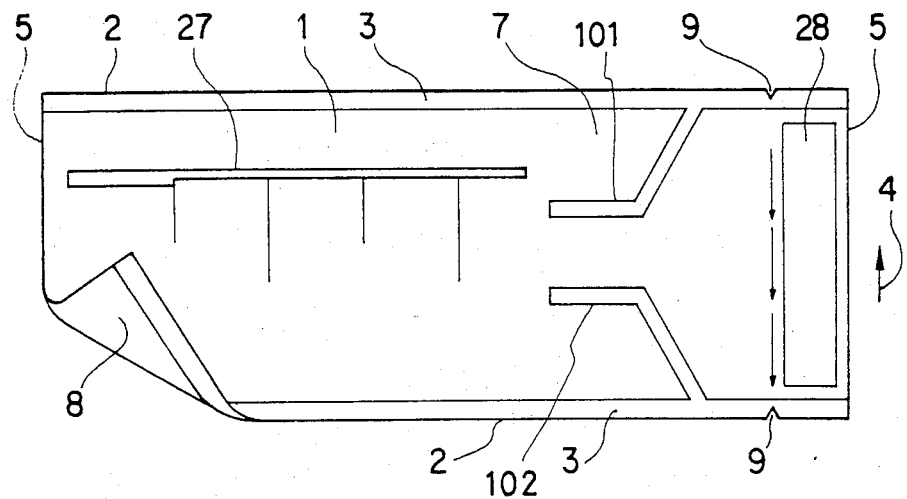
FIG. 14 is a plan view of another embodiment of the bag according to this invention in which one end of the bag is turned back for showing the lower surface as well as the upper one thereof.
Figure 15:
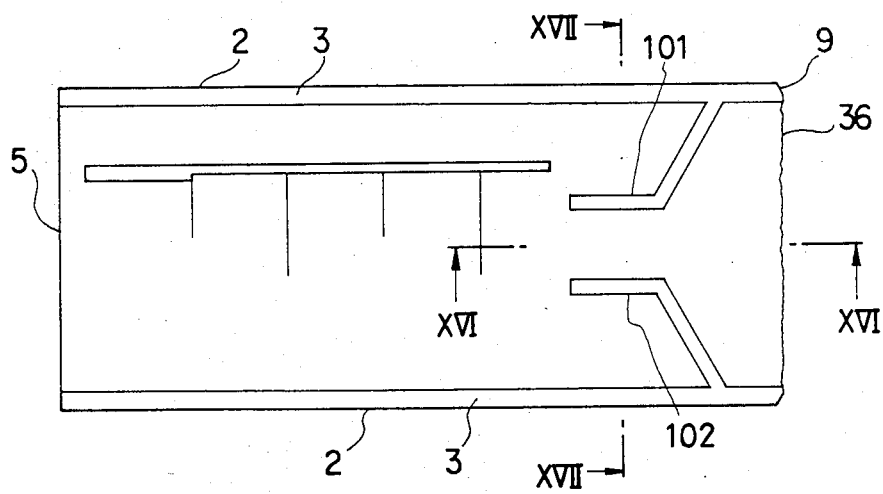
FIG. 15 is a plan view of the bag shown in FIG. 14 after opening the sealed side.
Figure 16:
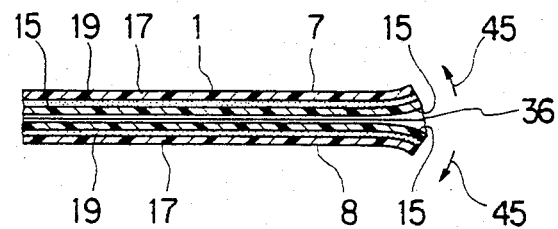
FIG. 16 is an enlarged cross sectional view taken along line XVI—XVI in FIG. 15.
Figure 17:
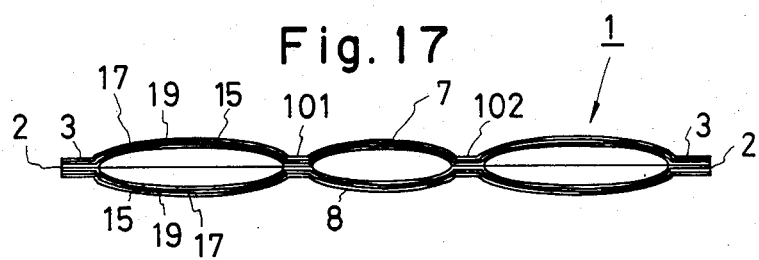
FIG. 17 is a cross sectional view along line XVII—XVII in FIG. 15.

If desired, one of the welds 101 and 102 may be cancelled from the bag 1 of FIG. 14. One of the welds 105 and 106, one of welds 107 and 108, or one of the welds 109 and 110 may be removed if necessary.

Although the bags 1, 60, 70 and 90 are made of the laminated tube 10, they can be made from known laminated film which is welded along the outer circumference thereof to constitute a tightly sealed bag. Further, the bag may be made of a two or more layered laminate.

As described above, since the bag according to the invention is made of a laminated tube or film prepared through extrusion molding, it can sufficiently have various properties required as the bag for mother's milk, such as cold resistance, water proofness, and strength. Furthermore, the bag is extended perpendicularly to the extrusion direction and comprises welds at the sides of the bag for tightly sealing the bag and notches formed on the welds and oriented to the extrusion direction for opening the side of the bag along the extrusion direction. Accordingly, the invention can provide a bag for mother's milk capable of maintaining the inside clean by the irradiation of gamma rays in the sealed state and can be opened with ease at one side just before containing the milk.

What is claimed is:

1. A bag for the preservation of mother's milk made of a laminated film or a laminated tube prepared by extrusion molding, said bag comprising:

(a) a first surface and a second surface which are joined together around a periphery comprising first to fourth edges to define a closed interior volume between said first and second surfaces which is at least substantially empty prior to use of the bag, said first and second surfaces having a first welded portion which is formed by welding said first surface to said second surface along said first edge perpendicular to the direction in which said first and second surfaces have been extruded;

(b) second and third welded portions formed by welding inner layers of said first and second surfaces so that said second welded portion extends inwardly from said first edge and the third welded portion extends inwardly from the second edge opposite to said first edge to form a funnel-shaped portion, whereby said second and third welded portions form a narrow passage for the milk and effect prevention of any reflux flow of milk to an outside of the bag; and (c) a notch which is provided on said first edge between the second welded portion and said third edge which extends parallel to said direction, the first welded portion having a width and the notch extending only part way through the first welded portion, the notch being directed in said direction.

2. The bag according to claim 1 in which said second and third welded portions comprise respective first portions extending respectively from said first edge and said second edge and respective second portions which are respectively connected to said first portions and directed towards said fourth edge extending oppositely to said third edge.

3. The bag according to claim 1 in which inner surfaces of the bag are in a sterilized state by treatment of gamma ray irradiation.

4. The bag according to claim 1 in which the laminated film or laminated tube comprises an inner layer made of transparent polyethylene, an outer layer made of transparent nylon, and an adhesive layer disposed between the inner layer and the outer layer.

5. The bag according to claim 4 in which the inner layer has a greater elongation rate than the elongation rate of the outer layer.

6. The bag according to claim 4 in which the first and second surfaces are transparent and the bag has a scale disposed on the outer layer for measuring the amount of mother's milk contained in said bag.

7. The bag according to claim 1 in which said funnel-shaped portion is located near the third edge to be opened.

8. The bag according to claim 1 and further comprising a closing means for reclosing an end of the bag after the end is opened and mother's milk is filled in said volume through the thus opened end.

9. The bag according to claim 8 in which said closing means comprises first, second and third elongate plate members, each of the first, second and third elongate plate members has first two edges opposite to each other and second two edges perpendicular to said first two edges of the elongate plate members and opposite to each other, each of the first edges of the first to third elongate plate members being shorter than each of the second edges of the first to third elongate plate members in their length, and the first elongate plate member is foldably connected along one of the second edges thereof with one of the second edges of the second elongate plate member and is foldably connected along one of the first edges thereof with one of the first edges of the third elongate plate member.

10. The bag according to claim 9 in which said closing means further comprises a fourth elongate plate member which has first two edges opposite to each other and second two edges perpendicular to said first two edges of the fourth elongate plate member and opposite to each other, the first two edges of the fourth elongate plate member being shorter than the second two edges of the fourth elongate plate member in their length, and said first elongate plate member is further connected foldably along the other one of the first edges thereof with one of the first edges of the fourth elongate plate member.

11. The bag according to claim 10 in which each of first and second elongate plate members has a length slightly greater than that of the third edge of the periphery and each of said third and fourth elongate plate members has a length greater than one-half of that of the third edge of the periphery.

12. The bag according to claim 9 in which each of said first, second, and third elongate plate members has a length slightly greater than that of the third edge of the periphery.

13. The bag according to claim 12 in which each of said first, second, and third elongate plate members is made of thick paper board.

14. The bag according to claim 1 in which the bag has a rectangular configuration defined by said first edge, said second edge which is perpendicular to said direction, said third edge and said fourth edge which is parallel to said direction, the bag having a fourth welded portion provided along said second edge.

15. The bag according to claim 1 in which the first and second surfaces are divided into a first trapezoidal-shaped bag portion and a second trapezoidal-shaped bag portion by fourth and fifth welded portions extending along a cutting line on both sides of the cutting line, which is oblique to and intersects said first and second edges and facilitates a separation of the first and second bag portions, said first bag portion has said funnel-shaped portion between the cutting line and the third edge and has said notch, the first bag portion further has another notch formed on the fourth welded portion for opening a triangle portion defined by the second edge and the cutting line, the second bag portion has another funnel-shaped portion provided between the cutting line and the fourth edge which extends parallel to said direction and has two notches formed on the first welded portion, one of the two notches of the second bag portion being positioned to open another triangle portion defined by the first edge and the cutting line and the other one of the two notches of the second bag portion being disposed between the fourth edge and the funnel-shaped portion of the second bag portion.

16. The bag according to claim 1, in which the first and second surfaces are divided into a first trapezoidal-shaped bag portion and a second trapezoidal-shaped bag portion by fourth and fifth welded portions extending along a cutting line on both sides of the cutting line, which is oblique to and intersects said third edge and said fourth edge which is parallel to said direction and facilitates a separation of the two bag portions, said first bag portion has said first welded portion, said funnel-shaped portion and said notch, said first bag portion further has another notch formed on the first welded portion between the fourth edge and the funnel-shaped portion, the second bag portion has another funnel-shaped portion provided between the third and fourth edges and two notches formed on a sixth welded portion provided along the second edge, one of the two notches of the second bag portion being positioned between said another funnel-shaped portion and the fourth edge and the other one of the two notches of the second bag portion being disposed between said another funnel-shaped portion and the third edge.

17. The bag according to claim 1 in which the bag has a configuration defined by said first edge and said second edge which is perpendicular to the direction, said third edge, said fourth edge which is parallel to the direction, a fifth edge extending parallel to said first edge from said fourth edge, and a sixth edge extending from said fifth edge to intersect said second edge, the bag having fourth to sixth welded portions provided respectively along said second, fifth, and sixth edges.

18. The bag according to claim 1 in which the bag has a configuration defined by said first edge, said second edge perpendicular to the direction, said third edge, said fourth edge which is parallel to the third edge, a fifth edge extending parallel to said first edge from said fourth edge, and a sixth edge extending from said fifth edge to intersect said second edge, the bag having fourth to seventh welded portions provided respectively along said second, fourth fifth, and sixth edges.

19. The bag according to claim 17 or 18 in which the bag has a discharge port for transferring mother's milk contained in the bag into a baby's bottle, the discharge port being defined by said first, fourth, and fifth edges and having another notch provided on the first welded portion.

20. The bag according to claim 1 and further comprising:
(a) first closing means for facilitating tearing of the notch, said first closing means being firmly fixed to an outer surface of one of said first and second surfaces in an end of the bag to be opened along said notch in order to supply the milk into the bag, after the end being opened, the thus opened end of the bag being rolled up at least one turn together with the first closing means, and
(b) a second closing means for maintaining the thus rolled up portion of the bag in rolled up state.

21. The bag according to claim 1 and further comprising a closing means comprising a first part and a second part, the first part having a first elongate plate member and a second elongate plate member, the second part having a third elongated plate member and a fourth elongate plate member, each of the first, second, third and fourth elongate plate members having first two edges opposite to each other and second two edges perpendicular to said first two edges of the elongate plate members and opposite to each other, the first two edges of the first to fourth elongate plate members being shorter than the second two edges of the first to fourth elongate members in their length, the first elongate plate member being foldably connected along one of the first edges thereof to one of the first edges of the second elongate plate member, the third elongate plate member being foldably connected along one of the first edges thereof to one of the first edges of the fourth elongate plate member, the first part being firmly fixed, before filling of the milk, to a nearly top end of the bag, whereby said top end of the bag may be torn off in order to open the bag, the second part being firmly fixed, after filling of the milk, to an outer surface of the bag which is rolled up together with the first part.

22. The bag according to claim 21 in which at least one of said first and second parts of the closing means is made of thick paper board.

23. The bag according to claim 21 in which said first part is made of thick paper board and said second part is made of transparent material.

24. The bag according to claim 23 in which said transparent material is a thermoplastic resin.

* * * * *